United States Patent [19]

Kobayashi et al.

[11] Patent Number: 4,724,199
[45] Date of Patent: Feb. 9, 1988

[54] SILVER HALIDE PHOTOGRAPHIC LIGHT SENSITIVE MATERIALS

[75] Inventors: Hidetoshi Kobayashi; Masaharu Toriuchi; Isamu Itoh, all of Kanagawa, Japan

[73] Assignee: Fuji Photo Film Co., Ltd., Kanagawa, Japan

[21] Appl. No.: 792,187

[22] Filed: Oct. 28, 1985

Related U.S. Application Data

[63] Continuation of Ser. No. 671,842, Nov. 15, 1984, abandoned.

[30] Foreign Application Priority Data

Nov. 15, 1983 [JP] Japan .................................. 58-214808

[51] Int. Cl.$^4$ .................... G03C 1/02; G03C 5/54; G03C 7/26
[52] U.S. Cl. .................................. 430/564; 430/217; 430/218; 430/542; 430/598; 430/955
[58] Field of Search ............... 430/598, 955, 218, 542, 430/217, 564

[56] References Cited

U.S. PATENT DOCUMENTS

| | | | |
|---|---|---|---|
| 3,728,113 | 4/1973 | Becker et al. | 430/223 |
| 4,232,107 | 11/1980 | Janssens | 430/218 |
| 4,358,525 | 11/1982 | Mooberry et al. | 430/598 |
| 4,358,532 | 11/1982 | Koyama et al. | 430/598 |
| 4,390,618 | 6/1983 | Kobayashi et al. | 430/955 |
| 4,435,495 | 3/1984 | Lau | 430/218 |

Primary Examiner—John E. Kittle
Assistant Examiner—Mukund J. Shah
Attorney, Agent, or Firm—Sughrue, Mion, Zinn, Macpeak, and Seas

[57] ABSTRACT

A silver halide photographic light-sensitive material containing, in at least one layer thereof, a compound capable of releasing a fogging agent upon an oxidation-reduction reaction with an oxidation product of a developing agent under an alkaline condition. The material has an increased sensitivity, an increased contrast and an accelerated development rate.

11 Claims, No Drawings

SILVER HALIDE PHOTOGRAPHIC LIGHT SENSITIVE MATERIALS

This is a continuation of application Ser. No. 671,842, filed Nov. 15, 1984, now abandoned.

FIELD OF THE INVENTION

This invention relates to silver halide photographic light-sensitive materials containing a compound capable of releasing a fogging agent upon an oxidation-reduction reaction with an oxidation product of a developing agent, i.e., a compound capable of imagewise releasing a fogging agent, in at least one layer thereof.

BACKGROUND OF THE INVENTION

In silver halide color photographic light-sensitive materials, it is well known that a development accelerator or a fogging agent is released from a certain kind of coupler during color development processing. U.S. Pat. No. 4,390,619 and Japanese Patent Application (OPI) Nos. 150845/82 and 50439/84 (British Patent Application No. 2,131,188A) (the term "OPI" as used herein refers to a "published unexamined Japanese patent application") disclose couplers which release fogging agents upon reacting with color developing agent oxidation products and demonstrate the effects to increase contrast or accelerate development brought about by the imagewise release of fogging agents. However, it is believed that these compounds are incapable of releasing a fogging agent in monochromatic development in which monochromatic developing agents, e.g., hydroquinone, methol, 3-pyrazolidone, etc., are used. Therefore, these known compounds cannot be employed in light-sensitive materials which are subjected to monochromatic development requiring high contrast and development acceleration, such as common monochromatic light-sensitive materials, color reversal light-sensitive materials, monochromatic light-sensitive materials for printing, monochromatic light-sensitive materials for X-rays, monochromatic light-sensitive materials having high resolving power, light-sensitive materials for a diffusion transfer process and the like. In order to heighten contrast or accelerate development in monochromatic development, it is desired to develop a compound which imagewise releases a fogging agent through monochromatic development.

Japanese Patent Application (OPI) No. 55332/75 or U.S. Pat. No. 4,435,495 makes some reference to such a compound, but the descriptions therein mainly relate to development inhibitor releasing compounds. There is no description therein as to either specific examples of such a compound or specific effects thereof.

SUMMARY OF THE INVENTION

A first object of this invention is to provide a silver halide photographic light-sensitive material which can produce high contrast.

A second object of this invention is to provide a silver halide light-sensitive material which can be rapidly developed under acceleration.

A third object of this invention is to provide a silver halide light-sensitive material having high sensitivity.

A fourth object of this invention is to provide a silver halide light-sensitive material which suffers from less color stain.

A fifth object of this invention is to provide a silver halide light-sensitive material excellent in color balance.

These objects of this invention have been met by a silver halide photographic light-sensitive material which contains, in at least one layer thereof, a fogging agent releasing compound which releases a fogging agent, under an alkaline condition, upon an oxidation-reduction reaction with an oxidation product of a developing agent during development processing.

DETAILED DESCRIPTION OF THE INVENTION

The fogging agent releasing compounds that are particularly useful in the present invention are represented by the following formulae (I) to (VI):

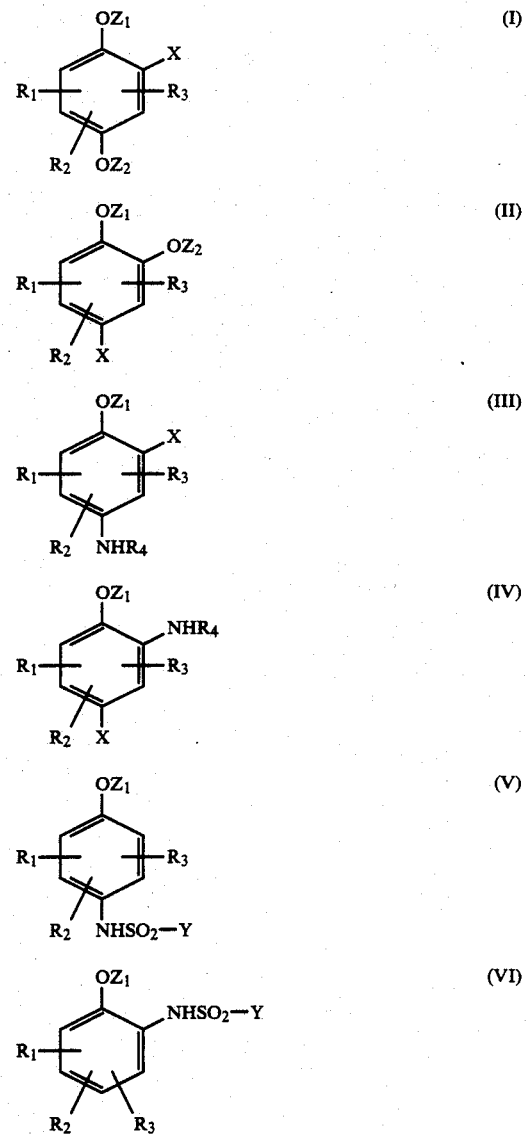

wherein $R_1$, $R_2$ and $R_3$, which may be the same or different, each represents a hydrogen atom, a halogen atom, an alkyl group, an aryl group, an alkoxy group, an aryloxy group, an alkylthio group, an arylthio group, a cyano group, an alkoxycarbonyl group, a carbamoyl group, a sulfamoyl group, a carboxyl group, a sulfo group, a sulfonyl group, an acyl group, a cyano group, a carbonamido group, a sulfonamido group or a heterocyclic group; or $R_1$ and $R_2$ are bonded to each other to form a benzene ring or a 5- to 7-membered heterocyclic ring; $R_4$ represents an alkyl group, an aryl group, an acyl group, a carbamoyl group, a sulfonyl group or a sulfamoyl group; $Z_1$ and $Z_2$, which may be the same or different, each represents a hydrogen atom or a group capable of being removed by hydrolysis under an alkaline condition; X represents a group which exhibits a fogging effect in a developing solution when released; and Y represents a group which exhibits a fogging effect in a developing solution when released as Y-$SO_2NH_2$ or its anion.

Typical examples of $Z_1$ or $Z_2$ include a hydrogen atom, an acyl group (e.g., acetyl, chloroacetyl, dichloroacetyl, trifluoroacetyl, benzoyl, p-nitrobenzoyl, etc.), a sulfonyl group (e.g., methanesulfonyl, benzenesulfonyl, etc.), an alkoxycarbonyl group (e.g., methoxycarbonyl, phenoxycarbonyl, etc.), a carbamoyl group (e.g., ethylcarbamoyl, phenylcarbamoyl, etc.), an oxalyl group (e.g., pyruvoyl, methoxalyl, phenyloxamoyl, etc.), as well as groups represented by the following formulae (VII) to (IX):

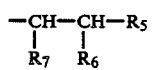
(VII)

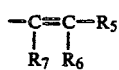
(VIII)

wherein $R_5$ represents an acyl group, a sulfonyl group, a cyano group, a carbamoyl group, a sulfamoyl group, an alkoxycarbonyl group, a nitro group, a carboxyl group, a sulfo group or an ammoniumyl group; and $R_6$ and $R_7$, which may be the same or different, each represents a hydrogen atom, an alkyl group or the same groups as those enumerated for $R_5$; or $R_5$ and $R_7$ may be bonded to each other to form a 5- to 7-membered ring.

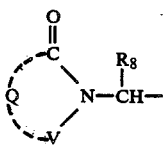
(IX)

wherein $R_8$ represents a hydrogen atom, an alkyl group or an aryl group; V represents

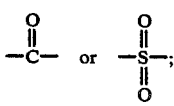

Q represents, when taken together with

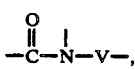

a non-metallic atomic group necessary to form a 5- or 6-membered ring.

Specific examples of the above-described groups (VII), (VIII) and (IX) are shown below:

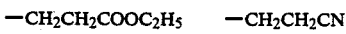

—CH$_2$CH$_2$COOC$_2$H$_5$  —CH$_2$CH$_2$CN

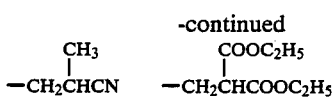

—CH$_2$CHCN  —CH$_2$CHCOOC$_2$H$_5$

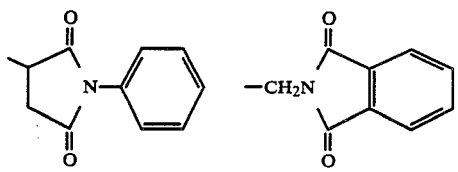

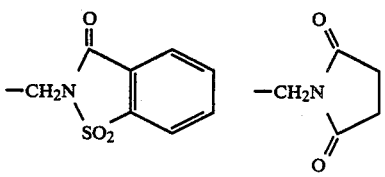

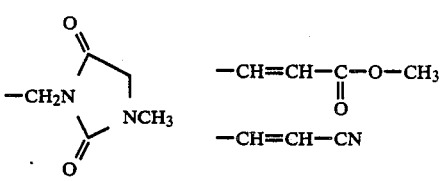

In the aforesaid formulae (I) to (IV), X preferably represents a group having the following formula (X):

$$\text{(TIME)}_m\text{L}_1\text{(L}_2)_n\text{A} \quad (X)$$

wherein TIME represents a so-called timing group which releases —$L_1$—$L_2)_n$A subsequently to the release of X; m represents 0 or 1; $L_1$ represents a group which is releasable for the release of X due to an oxidation-reduction reaction between the compounds (I) to (IV) and a developing agent oxidation product under an alkaline condition when m is 0, or a group releasable from TIME of the released X when m is 1; $L_2$ represents a divalent linking group; n represents 0 or 1; and A represents a group which substantially exhibits a fogging effect to a silver halide emulsion when X exists in a developing solution in the form of X⁻ or X—H.

Examples of the timing group, TIME, include those making use of intramolecular nucleophilic substitution as disclosed in U.S. Pat. No. 4,248,962 and Japanese Patent Application (OPI) No. 56837/82; and those making use of electron transfer through an intramolecular conjugation system as disclosed in U.S. Pat. No. 4,421,845, British Pat. No. 2,072,363A and Japanese Patent Application (OPI) Nos. 188035/82 and 98728/83; and the like. The TIME moiety also includes those involving multi-stage reactions.

The timing group represented by TIME in Japanese Patent Application (OPI) No. 56837/82 represents a group represented by a

portion being present in the following general formula:

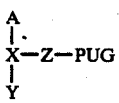

In the above general formula, A represents a component capable of reacting with the oxidation product of a color developing agent, PUG represents a photographically useful group, Y represents a nucleophilic group precursor, which may be connected with X to form a ring, and Z represents an electrophilic group. X is a group by which Y is three-dimensionally connected with Z, and it is connected with A at a position capable of being substituted with the oxidation product of the color developing agent. After the bond between A and X is cleaved, Y is changed to a nucleophilic group which causes an intramolecular nucleophilic displacement reaction with a ring closure with Z, whereby PUG is released.

The groups represented by X, Y and Z in the above-described general formula are groups capable of releasing the photographically useful group at a controlled timing, which are hereinafter called a timing group.

To explain the above-described compounds in view of their basic behavior, the A component can include any components capable of releasing an

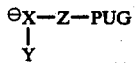

group upon reaction with the oxidation product of the color developing agent, examples of which components include the conventional couplers capable of forming a colored substance upon reaction with the oxidation product of the color developing agent and the compounds capable of forming a colorless substance upon reaction with the oxidation product of the color developing agent. The A component need not be stabilized (have a ballast group), but it may be stabilized with an oil-soluble group or an aliphatic grup. An

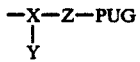

group is connected with the A component at a position where the A component reacts with the oxidation product of the color developing agent. Therefore, after the compound represented by the above-described general formula reacted with the oxidation product of the color developing agent, the

group is released. On the other hand, a part of the released

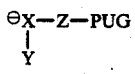

group is present as an

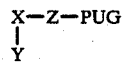

group through the conjugated system in X because of the occurrence of the delocalization of electrons. Consequently, Y which is the nucleophilic precursor is changed to the nucleophilic group which can cause an intramolecular nucleophilic displacement reaction with Z which is an electrophilic group, whereby PUG is ultimately relased. Thus, X is a group by which Y and Z are related with the three-dimensional position.

Further, the timing group represented by TIME in Japanese Patent Application (OPI) No. 188035/82 represents a group represented by a

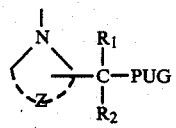

portion being present in the following general formula:

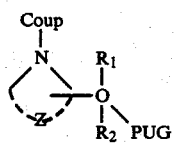

In the above formula, Coup represents a coupling component capable of coupling with the oxidation product of a color developing agent, $R_1$ and $R_2$ each represents a structural element capable of forming a 5-membered heterocyclic ring (inclusive of one forming a condensed ring), and Coup is connected with the heterocyclic ring at a position capable of being substituted with the oxidation product of the color developing agent. PUG represents a photographically useful group capable of being released, after the heterocyclic ring was released from Coup.

The timing group represented by TIME in Japanese Patent Application (OPI) No. 98728/83 is a group represented by a

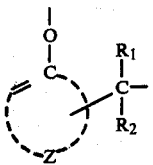

portion being present in the following general formula:

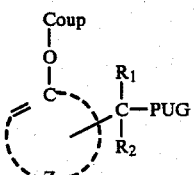

wherein Coup represents a coupling component capable of coupling with the oxidation product of a color developing agent, $R_1$ and $R_2$ each represents a hydrogen atom, an alkyl group or an aryl gorup, Z represents a structural element capable of forming a 6-membered heterocyclic ring including a condensed heterocyclic ring, and Coup is connected via the heterocyclic ring and the oxygen atom at a position capable of being substituted with the oxidation product of the color developing agent. PUG represents a photographically useful group capable of being released, after the heterocyclic ring connect to the oxygen atom was released from Coup.

British Pat. No. 2,072,363A includes examples of the timing group formulated in the following formula:

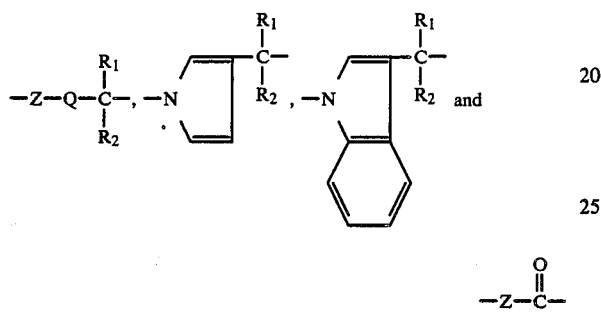

wherein the left-hand side is attached to the coupler group, Z is O, S or $R_1$, $R_2$ and $R_3$ are individually a hydrogen atom, alkyl or aryl group, Q is 1,2- or 1,4-phenylene or naphthylene group. The phenylene or naphthylene may have a substituent such as halogen atom, alkyl, alkoxy, —CN, —NO$_2$, —NHCOR or —COOR wherein R is alkyl.

Examples of $L_1$ include an aryloxy group, a heterocyclic oxy group, an arylthio group, a heterocyclic thio group, an azolyl group, etc. Specific examples of $L_1$ are shown below. The mark * indicates the bonding position to $+$TIME$+_m$.

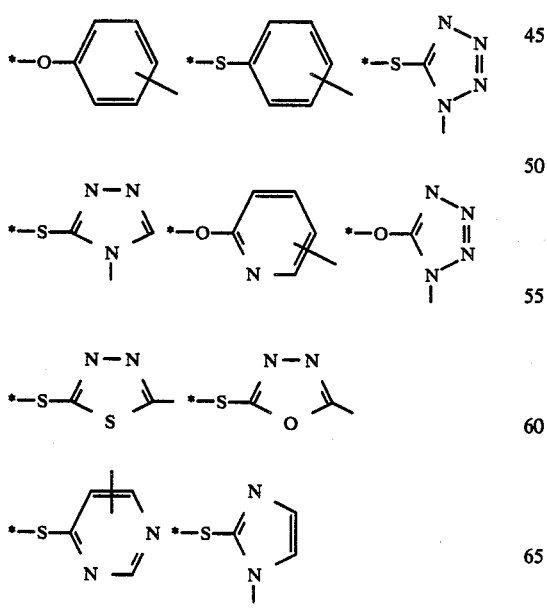

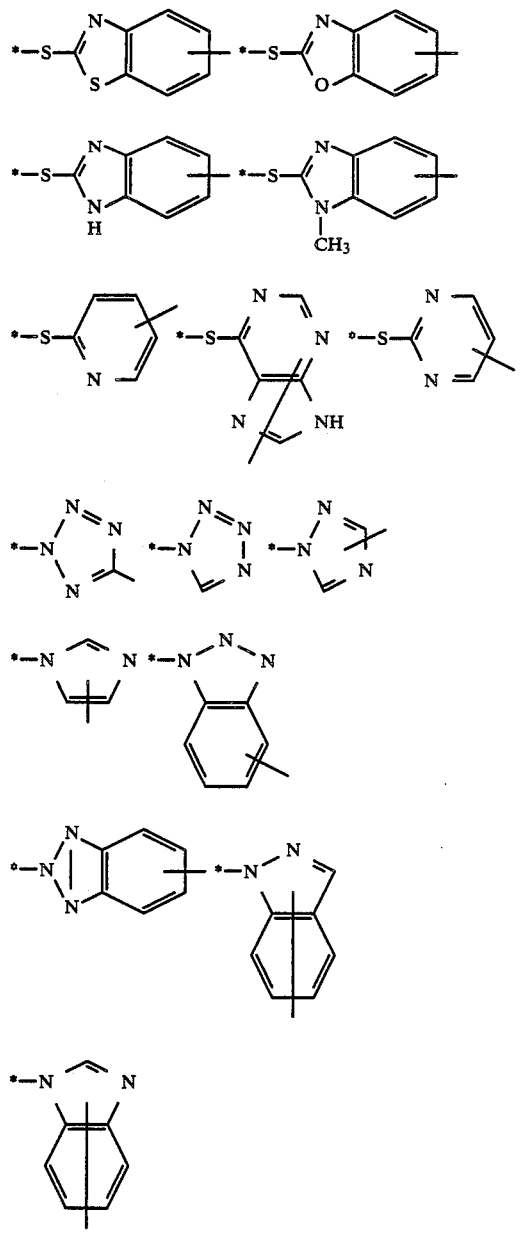

Examples of $L_2$ include an alkylene group, an alkenylene group, an arylene group, a divalent heterocyclic group, —O—, —S—, an imino group, —COO—, —CONH—, —NHCONH—, —NHCOO—, —SO$_2$NH—, —CO—, —SO$_2$—, —SO—, —NHSO$_2$NH—, etc., and combinations thereof.

A represents a reducing group (e.g., a group having the partial structure of hydrazine, hydrazide, hydrazone, hydroxylamine, polyamine, enamine, hydroquinone, catechol, p-aminophenol, o-aminophenol, aldehyde or acetylene), a group capable of acting on a silver halide during development to form a developable silver sulfide center (e.g., a group having the partial structure of thiourea, thioamide, thiocarbamate, dithiocarbamate, thiohydantoin, rhodanine, etc.) and quaternary salts (e.g., tetrazolium salts).

Particularly useful groups as A are represented by the formula (XI):

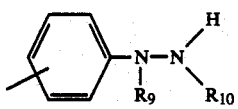
(XI)

wherein $R_9$ represents a hydrogen atom, an acyl group or an alkoxycarbonyl group; and $R_{10}$ represents an acyl group, a sulfonyl group, a carbamoyl group, an alkoxycarbonyl group, a sulfamoyl group, a thioacyl group, a thiocarbamoyl group or a heterocyclic group. The benzene ring in the formula (XI) and the benzene ring in $L_1$ in the formula (X) may overlap each other.

Specific examples of X are shown below:

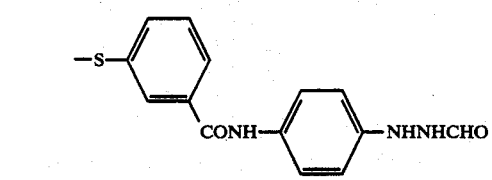

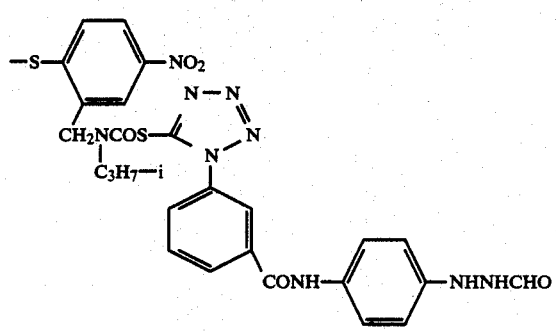

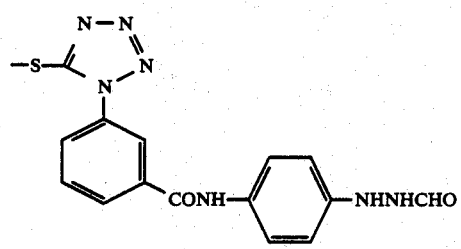

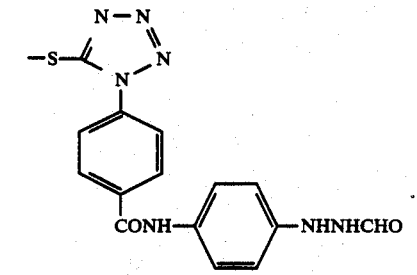

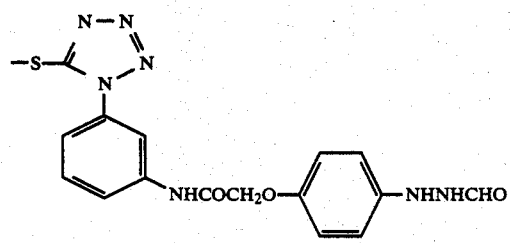

-continued

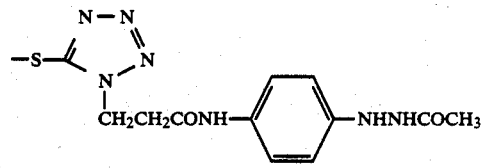

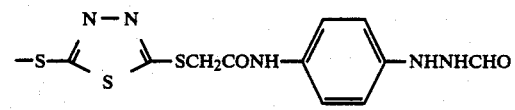

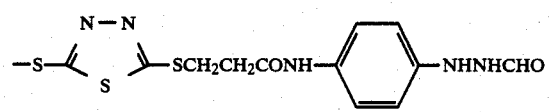

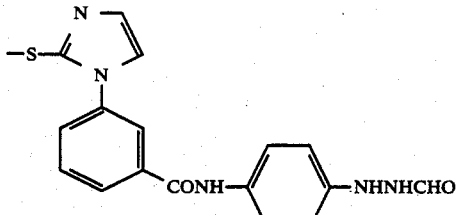

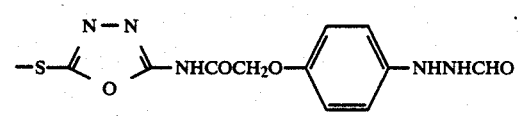

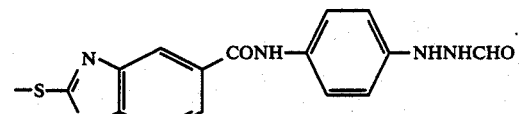

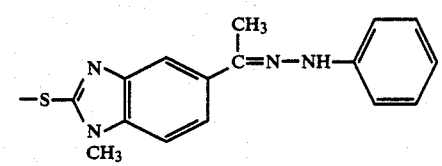

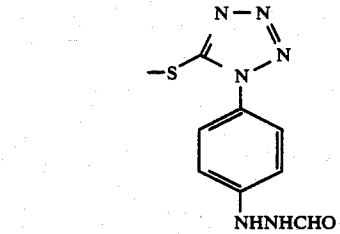

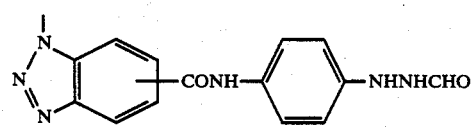

11
-continued
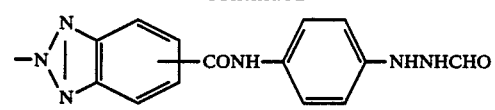
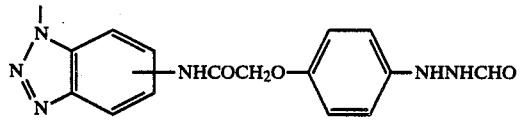
12
-continued
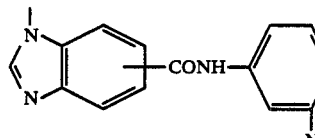
Y In the formulae (I) to (VI) as defined above apecifically includes the same groups as above enumerated for A.
Examples of the compounds (I) to (VI) according to the present invention are illustrated below:
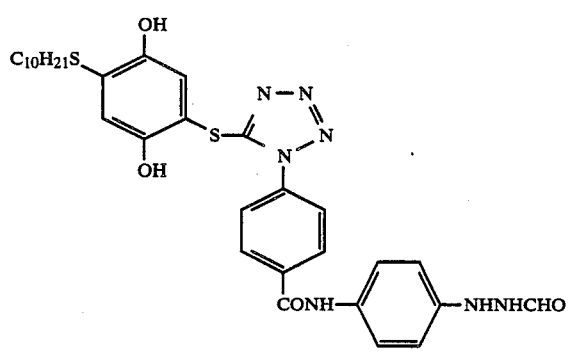
1.
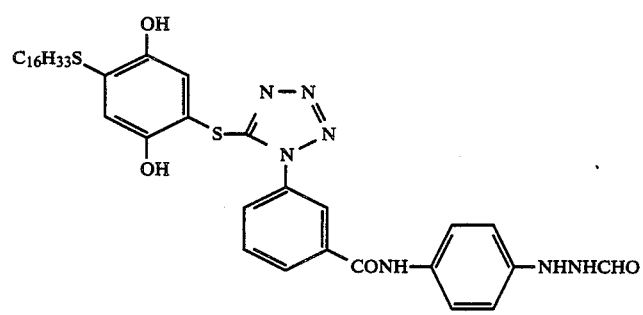
2.
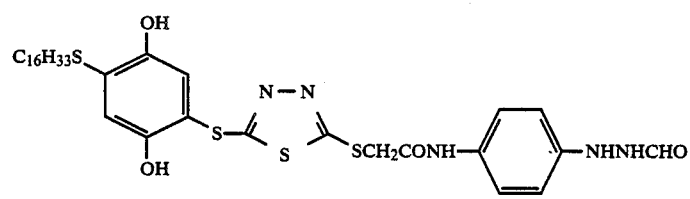
3.
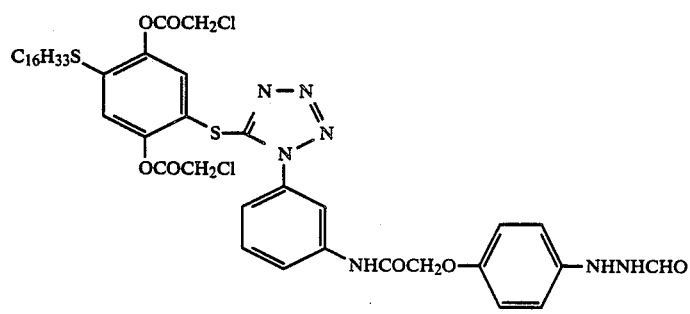
4.

-continued
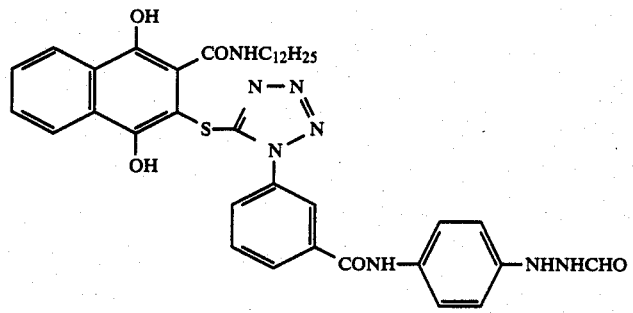
5.
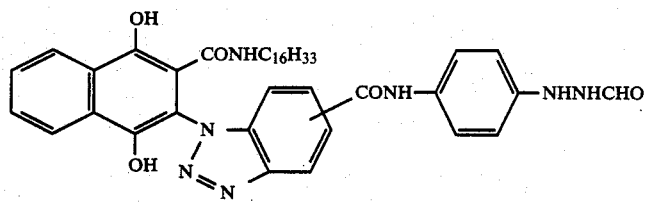
6.
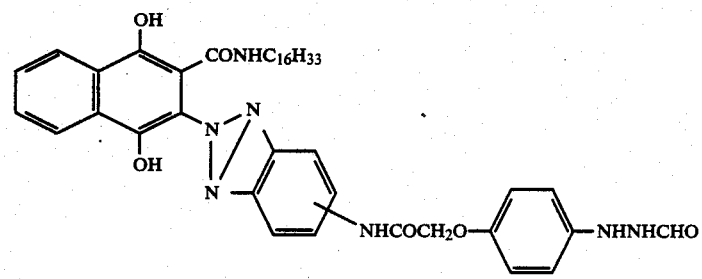
7.
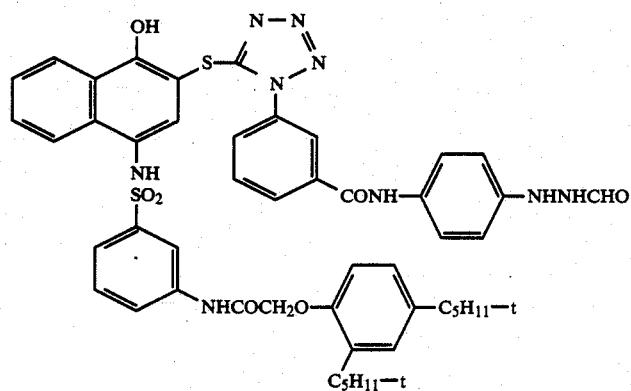
8.
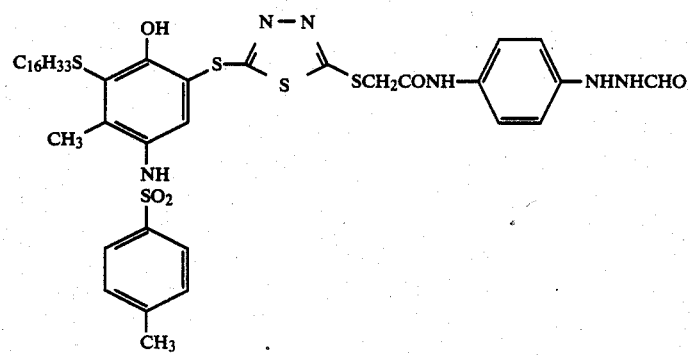
9.

-continued
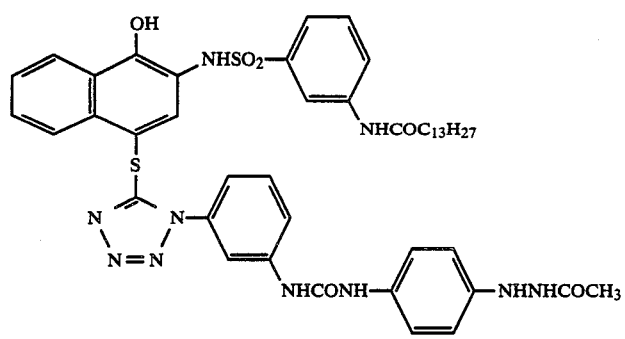
10.
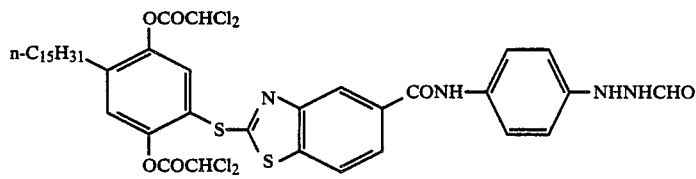
11.
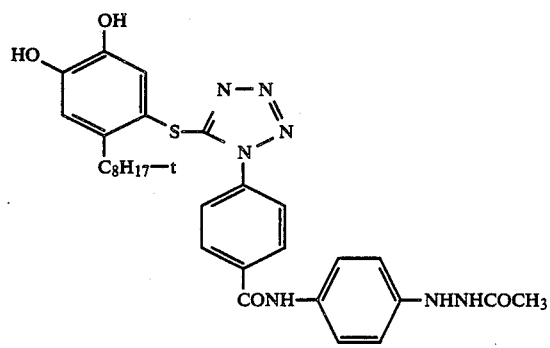
12.
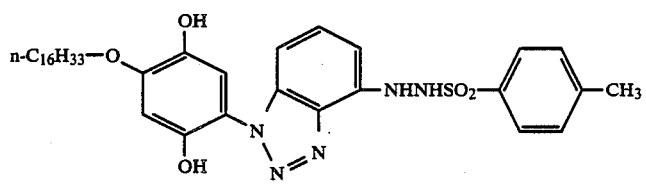
13.
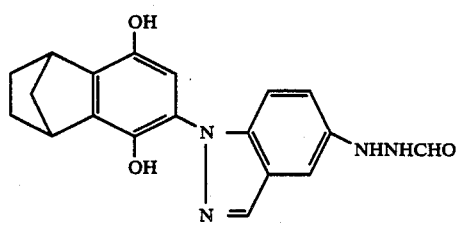
14.
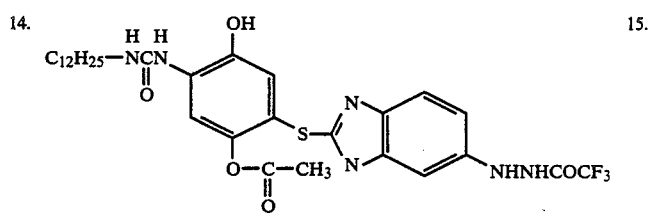
15.
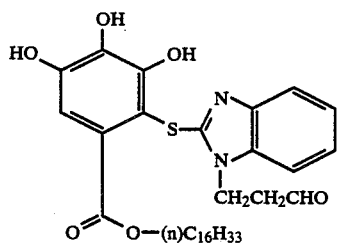
16.
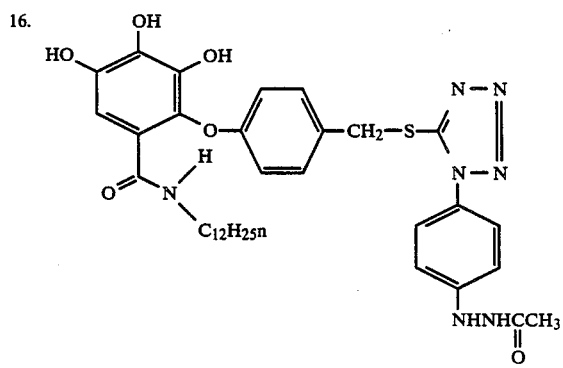
17.

17

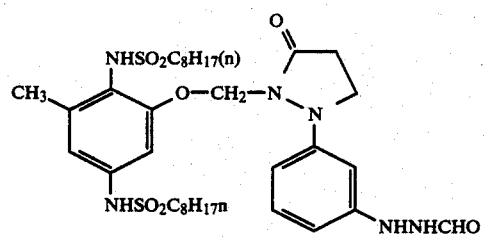

-continued

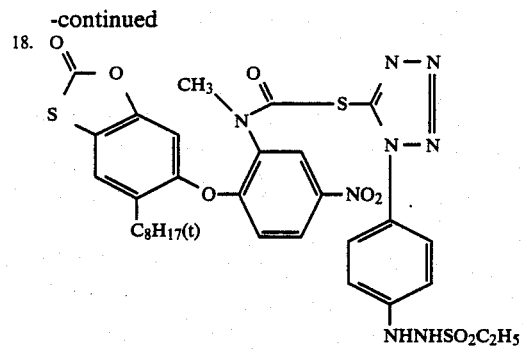

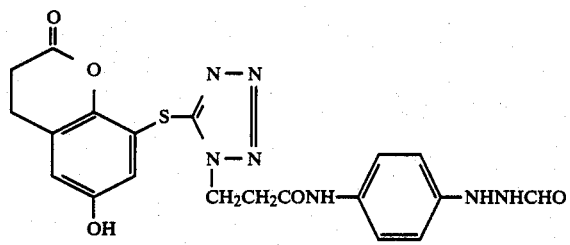

Synthesis examples of the compounds of the present invention are described below.

SYNTHESIS EXAMPLE 1

Synthesis of Compound No. 1

Synthesis of 2-[1-(4-Carboxyphenyl)-5-Tetrazolylthio]-5-n-Decyl-thiohydroquinone To a mixed solvent of 50 ml of acetonitrile and 20 ml of methanol were added 11.2 g (0.04 mol) of 2-n-decylthio-1,4-benzoquinone and 8.88 g (0.04 mol) of 1-(4-carboxyphenyl)-5-mercaptotetrazole, and the mixture was stirred at room temperature for 4 hours. The reaction mixture was filtered, and the resulting crude crystals were washed with 50 ml of methanol and 50 ml of acetone under heating, followed by filtration to obtain 12.7 g (63%) of the entitled compound. Melting point: 229° C. (with decomposition).

Synthesis of Compound No. 1

A solution of 4.3 g (0.021 mol) of dicyclohexylcarbodiimide in 10 ml of dimethylformamide was added dropwise at room temperature to a solution of 10 g (0.02 mol) of 2-[1-(4-carboxyphenyl)-5-tetrazolylthio]-5-n-decylthiohydroquinone and 3 g (0.021 mol) of N'-(4-aminophenyl)-N-formylhydrazine in 30 ml of dimethylformamide, and the mixture was stirred at the same temperature for 3 hours. After the thus precipitated dicyclohexylurea was removed, the reaction solution was poured into 50 ml of 50% methanol cooled at about 5° C., followed by filtration to obtain 2.3 g of first crude crystals. Fifty milliliters of ice-water was poured into the above filtrate to obtain 3.8 g of second crude crystals. The first and second crude crystals were dissolved in 30 ml of dimethylacetamide by heating, and 30 ml of methanol and 30 ml of water were added to the solution. The thus formed precipitate was filtered to obtain 4.2 g (33%) of Compound No. 1. Melting point: 210° C. (with decomposition).

Elementary Analysis for $C_{31}H_{37}N_7O_4S_2$:

|  | H | C | N |
|---|---|---|---|
| Calcd. (%): | 5.87 | 58.56 | 15.42 |
| Found (%): | 5.91 | 58.51 | 15.43 |

SYNTHESIS EXAMPLE 2

Synthesis of Compound No. 2

Synthesis of 5-Mercapto-1-{3-[4-(2-Formylhydrazino)Phenylcarbamoyl]Phenyl}Tetrazole In 50 ml of dimethylformamide were dissolved 11.1 g of 1-(3-carboxyphenyl)-5-mercaptotetrazole and 7.6 g of 4-(2-formylhydrazino)aniline, and a solution of 10.3 g of dicyclohexylcarbodiimide in 10 ml of dimethylformamide was added dropwise to the solution at 0° C. in a nitrogeneous atmosphere over about 30 minutes. After the addition, the mixture was stirred at room temperature for 3 hours. The precipitated dicyclohexylurea was separated by filtration, and the filtrate was added to 500 ml of ice-water while stirring. The thus precipitated crystals were filtered, washed with water and dispersed in 100 ml of hot methanol. The dispersion was allowed to cool to room temperature and filtered. The filtrate was washed with methanol to obtain 4.5 g of the desired compound. Melting point: 202° C. (with decomposition).

Synthesis of Compound No. 2

In 5 ml of dimethylformamide were dissolved in 0.73 g of 2-n-hexadecylthio-1,4-benzoquinone and 0.71 g of 5-mercapto-1-{3-[4-(2-formylhydrazino]phenylcarbamoyl]phenyl}tetrazole, and the mixture was stirred at room temperature in a nitrogen atmosphere for 5 hours. The reaction mixture was poured into 50 ml of ice-water while stirring, and the precipitated crude crystals were filtered and washed with water. The resulting crystals were dispersed in 50 ml of hot water, followed by allowing to cool to room temperature. The crystals were filtered and washed with methanol to obtain 0.84 g of Compound No. 2. Melting point: 198° C. (with decomposition).

| Elementary Analysis for $C_{37}H_{48}N_7O_4S_2$: | | | |
|---|---|---|---|
| | H | C | N |
| Calcd. (%): | 6.73 | 61.83 | 13.64 |
| Found (%): | 6.84 | 61.77 | 13.60 |

SYNTHESIS EXAMPLE 3

Synthesis of Compound No. 3

Synthesis of 2-Carboxymethylthio-5-Mercapto-1,3,4-Thiadiazole

In 200 ml of water were dissolved 15.0 g of 2,5-dimercapto-1,3,4-thiadiazole and 69 g of potassium hydroxide, and a solution of 13.9 g of bromoacetic acid in 30 ml of water was added thereto dropwise at room temperature. After the addition, the mixture was stirred at 60° C. for 1 hour, followed by allowing to cool to room temperature. The precipitated crystals were filtered and washed with water to obtain 18 g of the desired compound. Melting point: 161°–167° C.

Synthesis of 2-(2-Carboxymethylthio-1,3,4-Thiadiazol-5-ylthio)-5-Hexadecylthiohydroquinone In 30 ml of acetonitrile were dispersed 1.04 g of 2-carboxymethylthio-5-mercapto-1,3,4-thiadiazole and 1.82 g of 2-hexadecylthio-1,4-benzoquinone, and the dispersion was stirred at room temperature in a nitrogen atmosphere for 5 hours. The precipitated crystals were filtered and washed with acetonitrile to obtain 2.1 g of the desired compound. Melting point: 71°–76° C.

Synthesis of Compound No. 3

In 10 ml of dimethylformamide were dissolved 1.72 g of 2-(2-carboxymethylthio-1,3,4-thiadiazol-5-ylthio)-5-hexadecylthiohydroquinone and 0.45 g of 4-(2-formylhydrazino)aniline, and a solution of 0.62 g of dicyclohexylcarbodiimide in 2 ml of dimethylformamide was added thereto dropwise at 0° C. in a nitrogen atmosphere. After the addition, the mixture was stirred at room temperature for 3 hours, followed by filtration to remove dicyclohexylurea. The filtrate was poured into 30 ml of ice-water, and the precipitated crude crystals were filtered and dispersed in 30 ml of hot methanol. The dispersion was allowed to cool with stirring, and the crystals were filtered and washed with methanol to obtain 0.74 g of Compound No. 3. Melting point: 174°–178° C. (with decomposition).

| Elementary Analysis for $C_{33}H_{47}N_5O_4S_4$: | | | |
|---|---|---|---|
| | H | C | N |
| Calcd. (%): | 6.71 | 56.14 | 9.92 |
| Found (%): | 6.77 | 56.02 | 9.89 |

The compound according to the present invention can be used in an amount of $10^{-8}$ to 1 mol, preferably $10^{-8}$ to $10^{-2}$ mol and more preferably $10^{-6}$ to $10^{-4}$ mol, per mol of silver.

The light-sensitive materials according to the present invention can be development-processed by any known method, and conventional processing solutions can be used. Processing temperatures usually range from 18° C. to 50° C., but temperatures lower or higher than this range may also be employed. The light-sensitive materials of the present invention can be applied either to a monochromatic photographic development system to form silver images or to a color photographic development system to form color images according to the purpose.

The developing solution which can be used in monochromatic development can contain known developing agents. For example, developing agents are compounds represented by the following formulae (XII) and (XIII):

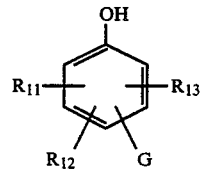

(XII)

wherein $R_{11}$, $R_{12}$ and $R_{13}$, which may be the same or different, each represents a hydrogen atom, a halogen atom, an alkyl group, an aryl group, an alkoxy group, an alkylthio group, an arylthio group, an acyl group, a carbonamido group, a sulfonamido group, a hydroxy group, or an amino group; and G represents a hydroxy group or an amino group (e.g., an amino group, a methylamino group, etc.).

The group G and the hydroxy group in the above formula (XII) are in an ortho- or para-position.

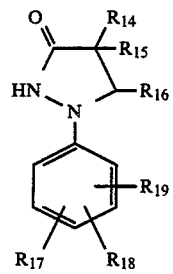

(XIII)

wherein $R_{14}$ and $R_{15}$, which may be the same or different, each represents a hydrogen atom or an alkyl group (e.g., methyl, ethyl, hydroxymethyl, etc.); $R_{16}$ represents a hydrogen atom, an alkyl group (e.g., methyl, ethyl, etc.), an alkoxycarbonyl group (e.g., ethoxycarbonyl, etc.) or an aryl group (e.g., phenyl, 2-methoxyphenyl, 4-hydroxyphenyl, etc.); and $R_{17}$, $R_{18}$ and $R_{19}$, which may be the same or different, each represents a hydrogen atom, a halogen atom, an alkyl group, an alkoxy group, a carbonamido group or a sulfonamido group.

In addition, ascorbic acid and heterocyclic compounds having such a structure as composed of condensed 1,2,3,4-tetrahydroquinone ring and indolene ring as described in U.S. Pat. No. 4,067,872 can also be used.

Specific examples of the developing agents which can be used in the present invention are shown below:

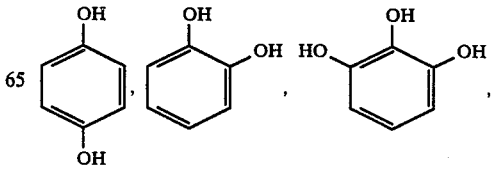

-continued

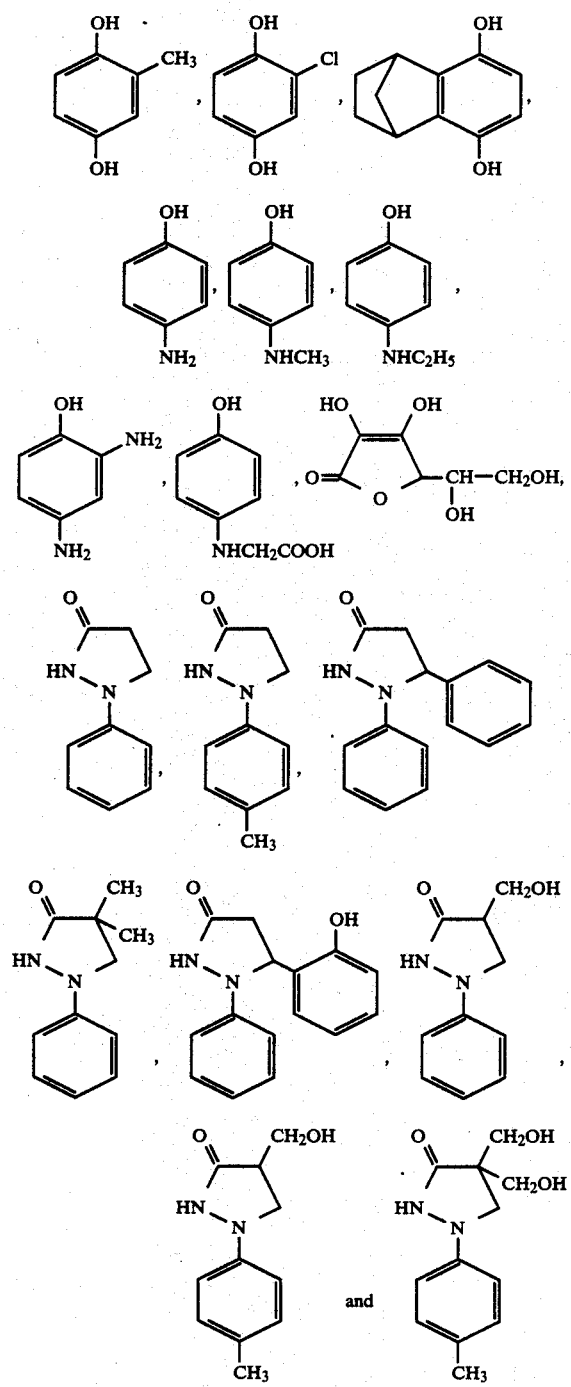

These developing agents can be used individually or preferably in combination of two or more of them. For example, a combination of hydroquinone and 3-pyrazolidone or a combination of hydroquinone and p-methylaminophenol, etc. can preferably be used.

The developing solution can generally contain conventional preservatives, alkali agents, pH-buffers, anti-foggants and the like, and can further contain, if necessary, dissolution assistant color controlling agents, development accelerators, surface active agents, defoamers, water softeners, hardeners, viscosity-imparting agents and the like.

The light-sensitive materials according to the present invention can be applied to the so-called lith development processing. The lith development processing is a development system wherein photographic reproduction of a line image or reproduction of a half-tone image by dots is effected by infectious development usually by using dihydroxybenzenes as developing agents in the presence of a low sulfite ion concentration. The details for the lith development are described in L. F. A. Mason, *Photographic Processing Chemistry*, pp 163–165, Focal Press (1966).

A unique development system wherein a developing agent is incorporated into the light-sensitive material, e.g., an emulsion layer, and the light-sensitive material is processed in an alkaline aqueous solution may also be employed. Hydrophobic developing agents can be dispersed in a latex and incorporated in an emulsion layer as described in *Research Disclosure*, No. 169, RD-16928. Such a development system may be combined with a silver salt stabilizing treatment using thiocyanates.

Fixing solutions are conventional and have commonly employed compositions.

Fixing agents which can be used include not only thiosulfates and thiocyanates but also organic sulfur compounds that are known to exhibit a fixing effect.

The fixing solution can contain a water-soluble aluminum salt as a hardener.

Formation of dye images can be effected in a usual manner. For example, methods for dye image formation include a negative-positive method as described in *Journal of the Society of Motion Picture and Television Engineers*, No. 61, pp 667-701 (1953); a color reversal method comprising processing a light-sensitive material in a developer containing a monochromatic developing agent to produce a negative silver image, subjecting the silver image to at least one uniform exposure or any appropriate fogging treatment, and subsequently performing color development; and a silver dye bleaching method comprising exposing a photographic emulsion layer containing dyes followed by development to form a silver image and bleaching the dyes using the silver image as a bleaching catalyst.

Color developing solutions generally comprise an alkaline aqueous solution containing a color developing agent. The color developing agent includes known primary aromatic amine developing agents, such as phenylenediamine (e.g., 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 3-methyl-4-amino-N-ethyl-N-$\beta$-methanesulfoamidoethylaniline, 4-amino-3-methyl-N-ethyl-N-$\beta$-methoxyethylaniline, etc.).

In addition, the color developing agents described in L. F. A. Mason, *Photographic Processing Chemistry*, pp 226–229, Focal Press (1966), U.S. Pat. Nos. 2,193,015 and 2,592,364, Japanese Patent Application OPI No. 64933/73, etc. can also be used.

The color developing solution can further contain pH-buffers, such as sulfites, carbonates, borates and phosphates of alkali metals, and development restrainers or anti-foggants, such as bromides, iodides and organic anti-foggants. Furthermore, according to necessity, the color developing solutions can contain water softeners; preservatives, e.g., hydroxylamine; organic solvents, e.g., benzyl alcohol and diethylene glycol; development accelerators, e.g., polyethylene glycol, quaternary ammonium salts and amines; color-forming couplers; competing couplers; fogging agents, e.g., sodium borohydride; developer assistants, e.g., 1-phenyl-3-pyrazolidone; viscosity-imparting agents; polycarboxylic acid series chelating agents described in U.S. Pat. No. 4,083,723; and antioxidants as described in West German Patent Application (OLS) No. 2622950.

After color development, the photographic emulsion is usually subjected to bleaching. Bleaching may be carried out simultaneously with fixing, or these processes may be carried out separately. Examples of bleaching agents which can be used include compounds of polyvalent metals, e.g., Fe (III), Co (III), Cr (VI), Cu (II), etc.; peroxy acids, quinones, nitroso compounds and the like. More specifically, usable bleaching agents include ferrocyanides; bichromates; complex salts formed by Fe (III) or Co (III) with aminopolycarboxylic acids, e.g., ethylenediaminetetraacetic acid, nitrilotriacetic acid, 1,3-diamino-2-propanol tetraacetic acid, etc., or organic acids, e.g., citric acid, tartaric acid, malic acid, etc.; persulfates and permanganates; nitrophenol; and the like. Of these, potassium ferricyanide, sodium(ethylenediaminetetraacetato)ferrate (III) and ammonium(ethylenediaminetetraacetato)ferrate (III) are particularly useful. The (ethylenediaminetetraacetato)iron (III) complexes are useful in both an independent bleaching solution and a combined bleach-fix bath.

The bleaching solution or the bleach-fix bath can contain bleach accelerating agents as described in U.S. Pat. Nos. 3,042,520 and 3,241,966 and Japanese Patent Publication Nos. 8506/70 (British Pat. No. 1,150,466) and U.S. Pat. No. 3,578,454, thiol compounds as described in Japanese Patent Application (OPI) No. 65732/78, and other various additives.

The compounds of the present invention can be applied to any type of light-sensitive material as long as they are capable of causing an oxidation-reduction reaction between the compounds of the present invention and an oxidation product of a developing agent, but in the most preferred embodiment, they can be applied to color diffusion transfer light-sensitive materials in which an alkaline processing solution is developed or heat developable color light-sensitive materials which are developable by heat, such as those described in Japanese Patent Application (OPI) No. 58543/83.

The light-sensitive silver halide emulsion which can be used in combination with the compounds of the present invention is a hydrophilic colloidal dispersion of silver chloride, silver bromide, silver iodobromide, silver iodochlorobromide or a mixture thereof. The halogen composition can be selected according to the end use and processing conditions of the light-sensitive material. Especially preferred silver halides are silver bromide, silver iodobromide and silver iodochlorobromide containing 10 mol% or less of iodide and 30 mol% or less of chloride.

Any of conventionally known silver halide emulsions can be used in the light-sensitive materials of the present invention. For example, negative emulsions which form a latent image predominantly on the surface of silver halide grains or direct reversal emulsions can be used.

The silver halide emulsions described in *Research Disclosure*, No. 22534 (1983) can also preferably be used.

The latter emulsions include those in which a latent image is predominantly formed in the interior of silver halide grains and previously fogged direct reversal emulsions.

The silver halide emulsions in which a latent image is formed in the interior of the silver halide grains which can be used in the present invention with advantage include conversion type emulsion, core-shell type emulsions and emulsions containing different kinds of metals.

Nucleating agents for the above-described emulsions typically include hydrazines, hydrazides, hydrazones, quaternary salt compounds, sensitizing dyes having a nucleating substituent in the molecule thereof as disclosed in U.S. Pat. No. 3,718,470 and thiourea-connected acylhydrazine compounds.

Color sensitivities of th silver halide emulsions which can be used in the present invention can be enlarged by spectral sensitization if necessary. The sensitizers which can be used for spectral sensitization include cyanine dyes, merocyanine dyes and the like.

The compounds of the present invention can also be used in combination with a color-donating compound. As is well known in the art, the color-donating compound is negative or positive and, when processed in an alkaline processing solution, is initially mobile or immobile in a photographic element.

Useful negative dye image-donating compounds include couplers capable of forming or releasing dyes upon reacting with an oxidized color developing agent. Specific examples of the negative dye image-donating compounds are given in U.S. Pat. No. 3,227,550 and Canadian Pat. No. 602,207.

Preferred negative dye image-donating compounds are dye-releasing redox compounds capable of releasing dyes upon reacting with a developing agent in an oxidized state or an electron transfer agent. Specific examples of such redox compounds are described in U.S. Pat. Nos. 4,055,428, 4,336,322 and 3,351,673. The immobile positive dye image-donating compounds include those which release diffusible dyes during a photographic processing under an alkaline condition without receiving an electron (i.e., without being reduced) or after receipt of at least one electron (i.e., after being reduced).

Further, positive dye image-donating compounds that are mobile from the beginning under an alkaline photographic processing condition include color developing agents and are specifically described in U.S. Pat. Nos. 3,857,855, 3,880,658, 3,935,262 and 3,935,263.

Furthermore, dye-releasing redox compounds having a dye moiety wherein light absorption is temporarily shifted in a light-sensitive element can also be used as a kind of dye precursor in combination with the compounds of the present invention.

The positive color-donating compounds may further be used in combination with anti-diffusible electron-donors well known as ED, which are specifically described in U.S. Pat. No. 4,278,750, etc.

The processing solution which can be used for processing the photographic light-sensitive materials according to one embodiment of the present invention suitably contains a base such as sodium hydroxide, potassium hydroxide, sodium carbonate, sodium phosphate, etc. and has a pH of about 9 or more, preferably 11.5 or more. The processing solution may contain an antioxidant, such as sodium sulfite, ascorbates, piperidinohexose reductone, etc., and a silver ion concentration controlling agent, such as potassium bromide. The processing solution can further contain a thickener such as hydroxyethyl cellulose, sodium carboxymethyl cellulose, etc.

The alkaline processing solution can further contain a compound which accelerates development or diffusion of dyes, such as benzyl alcohol.

Light-sensitive materials which can be used for reproduction of natural colors by subtractive color photography comprise at least one combination of an emulsion having a selective spectral sensitivity in a certain wavelength region and a dye image-donating compound having selective spectral absorption in the same wavelength region.

In particular, a combination of a blue-sensitive silver halide emulsion and a yellow dye-donating compound, a combination of green-sensitive emulsion and a magenta dye-donating compound and a combination of a red-sensitive emulsion and a cyan dye-donating compound are useful. These combination units of emulsions and dye-releasing redox compounds may be coated in layers in such a manner that the layer containing each combination unit faces each other or may be coated in one layer in which the dye-releasing redox compound and silver halide grains are present in the same grains.

A scavenger for an oxidized developing agent can be used in various intermediate layers in the photographic element of the present invention. Suitable compounds as the scavenger are described in *Research Disclosure*, No. 151 (November, 1976).

A parting layer may be provided between an intermediate layer and a layer containing the color-donating compound as described in U.S. Pat. No. 4,267,250. Further, the intermediate layer can contain a silver halide emulsion as described in U.S. Pat. No. 4,323,635.

Conventional mordant layer, neutralization layer, neutralization rate controlling layer (i.e., timing layer), processing compositions and the like which can be used in the present invention when the light-sensitive materials of the present invention are applied to a color diffusion transfer process are, for example, those described in U.S. Pat. No. 4,268,625.

Polymer mordants which can be used in the light-sensitive materials of the present invention include polymers having secondary and tertiary amino groups, a nitrogen-containing heterocyclic moiety, or a quaternary cation group thereof and having a molecular weight of more than 5,000, preferably more than 10,000.

More specifically, the polymer mordants can include a vinylpyridine polymer, a vinylpyridinium cation polymer, a vinylimidazolium cation polymer, a polymer mordant crosslinkable with gelatin, etc., an aqueous sol type mordant, a water-insoluble mordant, and a reactive mordant capable of covalently bonding with dyes as disclosed in U.S. Pat. Nos. 4,168,976 and 4,201,840.

An image-receiving layer for mordanting azo dyes having a chelating group is preferably a mordant layer or a layer adjacent thereto into which a transition metal ion and a polymer capable of immobilizing said transition metal ion are incorporated.

It is advantageous in view of broadening an allowable temperature range for processing to use a polymer acid layer protected with a temporary blocking layer by which the neutralization period can be shortened at high processing temperatures, such as a fused latex polymer layer or a lactone ring-containing polymer layer.

The present invention will now be illustrated in greater detail with reference to non-limiting examples.

EXAMPLE 1

An integrated type light-sensitive material for a color diffusion transfer process, a cover sheet and a processing solution were prepared as follows:

Preparation of Light-Sensitive Sheet

Onto a polyethylene terephthalate trnasparent support were coated the following layers (1) to (12) in this order to prepare Light-Sensitive Sheets 1 to 4.

(1) An image-receiving layer containing 3.0 g/m$^2$ of copoly[styrene-N-vinylbenzyl-N-methyl-piperidinium chloride] and 3.0 g/m of gelatin.
(2) A white reflecting layer containing 20 g/m$^2$ of titanium dioxide and 2.0 g/m$^2$ of gelatin.
(3) A light-screening layer containing 2.0 g/m$^2$ of carbon black and 1.0 g/m$^2$ of gelatin.
(4) A layer containing $2\times10^{-4}$ mol/m$^2$ of the following cyan dye-donating compound, $2\times10^{-4}$ mol/m$^2$ of Compound A (ED compound), 0.1 g/m$^2$ of N,N-diethyllaurylamide and 0.8 g/m$^2$ of gelatin.

Cyan dye-donating compound:

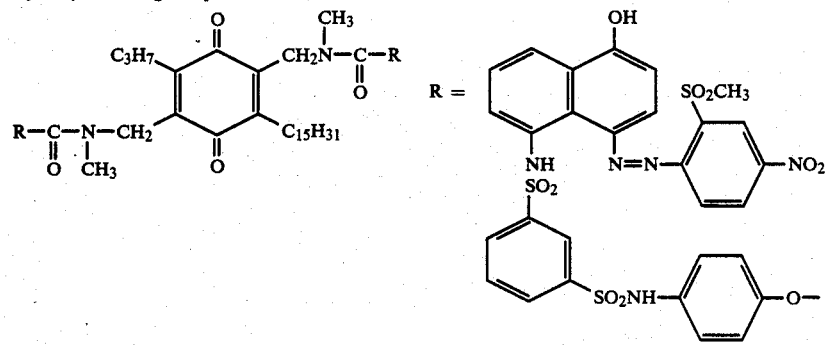

Compound A (ED Compound):

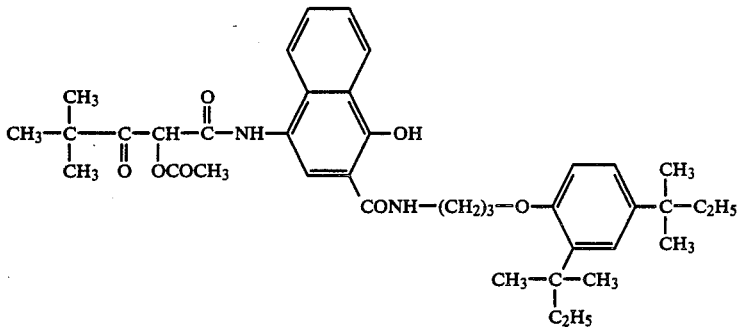

(5) A layer containing a red-sensitive silver bromide emulsion in an amount of 0.6 g/m² as silver, 5×10⁻⁵ mol/mol-Ag of the compound indicated in Table 1, 0.01 g/m² of N,N-diethyllaurylamide and 0.6 g/m² of gelatin.

(6) A layer containing 0.5 g/m² of 2,5-di-t-pentadecyl-hydroquinone and 0.4 g/m² of gelatin.

(7) A layer containing 3×10⁻⁴ mol/m² of a magenta dye-donating compound having the following structure, 3×10⁻⁴ mol/m² of the ED Compound A, 0.1 g/m² of N,N-diethyllaurylamide and 0.8 g/m² of gelatin.

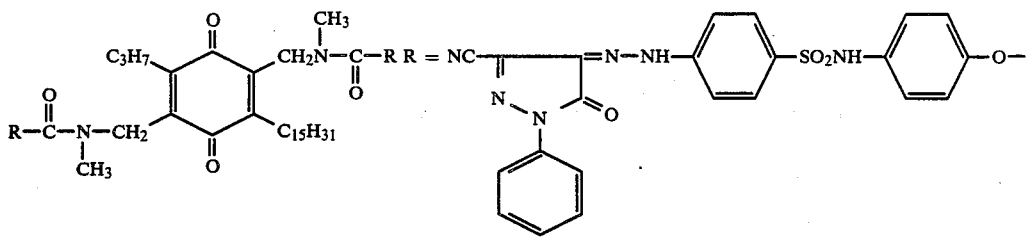

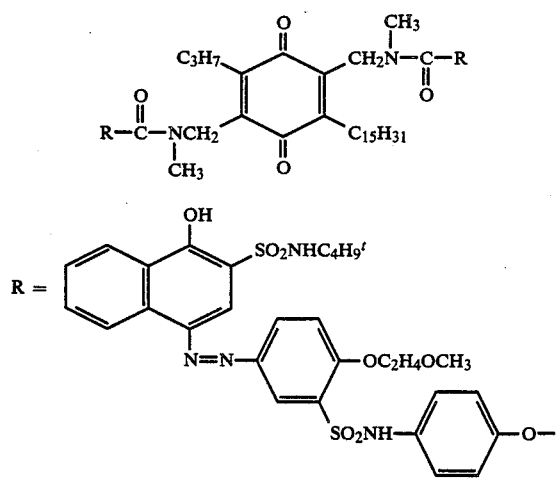

(8) A layer containing a green-sensitive silver bromide emulsion in an amount of 0.6 g/m² as silver, 5×10⁻⁵ mol/mol-Ag of a compound indicated in Table 1, 0.01 g/m² of N,N-diethyllaurylamide and 0.6 g/m² of gelatin.

(9) The same layer as layer (6).

(10) A layer containing 3×10⁻⁴ mol/m² of a yellow dye-donating compound having the following structure, 3×10⁻⁴ mol/m² of ED Compound A, 0.1 g/m² of N,N-diethyllaurylamide and 0.8 g/m² of gelatin.

(11) A layer containing a blue-sensitive silver bromide emulsion in an amount of 0.6 g/m² as silver, 3×10⁻⁵ mol/mol-Ag of a compound indicated in Table 1, 0.01 g/m² of N,N-diethyllaurylamide and 0.8 g/m² of gelatin.

(12) A layer containing 4×10⁻⁴ mol/m² each of the ultraviolet absorbents having the following structures, 0.02 g/m² of tris(2-ethylhexyl)phosphate and 1.0 g/m² of gelatin.

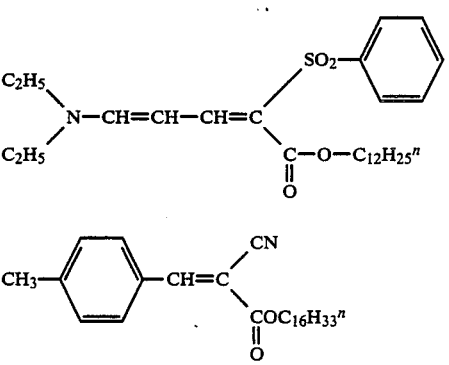

Preparation of Cover Sheet

Onto a polyethylene terephthalate transparent support were coated the following layers (1') to (3') in this order to prepare a cover sheet.

(1') A layer containing 22 g/m² of an acrylic acid/butyl acrylate copolymer (80:20 by weight) and 0.44 g/m² of 1,4-bis(2,3-epoxypropoxy)-butane.

(2') A layer containing 3.8 g/m² of acetyl cellulose having such an acetyl value that hydrolysis of 100 g sample forms 39.4 g of acetyl group, 0.23 g/m² of a methanol ring cleavage product of a styrene/maleic anhydride copolymer (60:40 by weight; molecular weight=ca. 50,000) and 0.154 g/m² of 5-(2-cyano-1-methylethylthio)-1-phenyltetrazole.

(3') A 2 micron-thick layer formed by coating a mixture consisting of a styrene/n-butyl acrylate/acrylic acid/N-methylacrylamide copolymer latex (49.7:42.3:3:5 by weight) and a methyl acrylate/acrylic acid/N-methylolacrylamide copolymer latex (93:4:3 by weight) at a mixing proportion of 6:4 on a solid basis.

The increase in contrast is believed to be brought about by a great increase in the rate of silver development.

TABLE 1

| Light-Sensitive Sheet | Compound No. | $D_{max}$ | | | $D_{min}$ | | | Gamma* | | | Relative Sensitivity S-0.2** | | | Remark |
|---|---|---|---|---|---|---|---|---|---|---|---|---|---|---|
| | | B | G | R | B | G | R | B | G | R | B | G | R | |
| 1 | blank | 1.60 | 2.20 | 2.31 | 0.20 | 0.20 | 0.32 | 0.8 | 0.9 | 0.9 | 0 | 0 | 0 | Comparison |
| 2 | 4 | 1.59 | 2.15 | 2.27 | 0.20 | 0.20 | 0.32 | 1.5 | 1.6 | 1.7 | +0.30 | +0.37 | +0.41 | Invention |
| 3 | 12 | 1.59 | 2.10 | 2.19 | 0.20 | 0.21 | 0.32 | 1.4 | 1.4 | 1.5 | +0.22 | +0.29 | +0.29 | " |
| 4 | 1 | 1.54 | 2.15 | 2.26 | 0.20 | 0.20 | 0.32 | 1.6 | 1.6 | 1.7 | +0.31 | +0.39 | +0.40 | " |

Note:
*A slope between two points of $D_{max} - 0.2$ and $D_{min} + 0.2$
**$\Delta\log E$ of the point of $D_{max} - 0.2$; The value for Light-Sensitive Material 1 (Comparison) was taken as zero. The greater the value, the higher the sensitivity.

| Composition of Processing Solution | |
|---|---|
| 1-p-Tolyl-4-hydroxymethyl-4-methyl-3-pyrazolidone | 10 g |
| Methylhydroquinone | 0.3 g |
| 3-Methylbenzotriazole | 3.5 g |
| Anhydrous sodium sulfite | 0.2 g |
| Sodium carboxymethyl cellulose | 58 g |
| Potassium hydroxide (28% aqueous solution) | 200 ml |
| Benzyl alcohol | 1.5 ml |
| Carbon black | 150 g |
| Water to make | 685 ml |

Each of the thus prepared Light-Sensitive Sheets 1 to 4 was exposed through a continuous gradation wedge, and a combination of the exposed light-sensitive sheet, the cover sheet and the processing solution was subjected to development-processing with an aid of a pair of pressure rollers. After 1 hour, color densities were measured by means of a densitometer to read $D_{max}$, gamma and sensitivity. The results obtained are shown in Table 1.

As is apparent from Table 1, it can be seen that the light-sensitive materials according to the present invention exert remarkable effects to greatly increase sensitivity and contrast without a substantial reduction in $D_{max}$.

EXAMPLE 2

Light-Sensitive Sheets 5 to 8 were prepared according to the following manner.

Preparation of Light-Sensitive Sheet

Onto a polyethylene terephthalate transparent support were coated the following layers (1) to (7) in this order.

(1) to (3): The same as the layers (1) to (3) as described in Example 1.

(4) A layer containing 0.44 g/m² of a cyan dye-releasing redox compound having the following structure, 0.09 g/m² of tricyclohexyl phosphate, 0.008 g/m² of 2,5-di-t-pentadecylhydroquinone and 0.8 g/m² of gelatin.

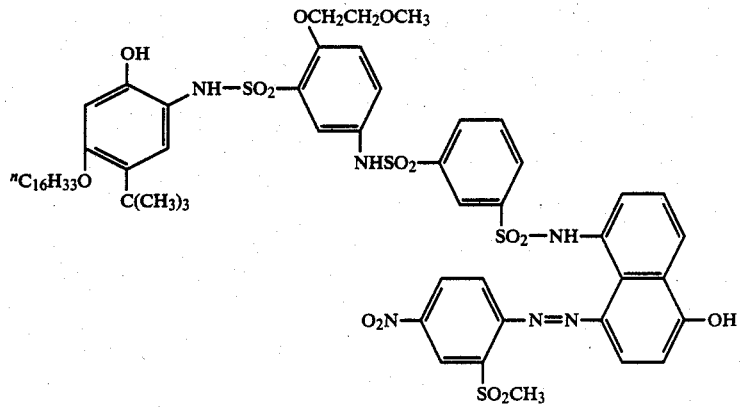

(5) A red-sensitive emulsion layer containing a red-sensitive direct positive silver bromide emulsion of the type that a latent image is formed in the interior of the grains in an amount of 1.03 g/m² as silver, 0.01 mg/m² of a nucleating agent having the followng structure, 0.13 g/m² of sodium 2-sulfo-5-n-pentadecylhydroquinone, a compound indicated in Table 2 in an amount of 1×10⁻⁵ mol per mol of silver and 0.01 g/m² of N,N-diethyllaurylamide.

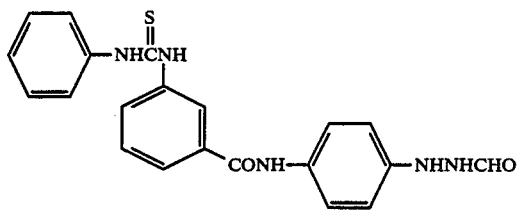

(6) A layer containing 0.43 g/m² of 2,5-di-t-pentadecyl-hydroquinone, 0.1 g/m² of trihexyl phosphate and 0.4 g/m² of gelatin.

(7) A protecting layer containing 0.5 g/m² of gelatin and 0.02 g/m² of triacryloyltriazine.

Each of the thus prepared Light-Sensitive Sheets 5 to 8 was exposed to light, subjected to development-processing and measured in density in the same manner as in Example 1. The results obtained in the photographic properties are shown in Table 2. Further, the rate of dye transfer was also measured as an indication of the rate of silver development of the light-sensitive sheet, and the results obtained are also shown in Table 2. The rate of dye transfer was obtained by subjecting the unexposed light-sensitive sheet to development-processing and tracing changes in density by means of a Macbeth densitometer, and was expressed in terms of time requiring to reach 50% of the density after 10 minutes.

As is apparent from Table 2, the light-sensitive materials according to the present invention exhibited noticeable effects to increase sensitivities and rates of development.

agent) were added to a 5% gelatin solution to prepare a coating composition for an insensitive uppler layer.

The aforesaid coating composition for a light-sensitive silver halide emulsion layer and the coating composition for an insensitive upper layer were coated on a polyethylene terephthalate support by a simultaneous coating method. The resulting sample had a silver coverage of 3.0 g/m² and the dry thickness of the insensitive upper layer was 1.0μ.

Each sample was exposed to white tungsten light for 8 seconds through a gradient wedge having a difference in gradation of 0.1.

Further, a commercially available gray contact screen (150 lines/inch) was placed in close contact with each sample and exposed to white tungsten light for 10 seconds through a gradient wedge having a difference in gradation of 0.1, thereby to form a dot image.

The thus exposed sample was developed for 20 seconds using a developing solution having the following composition at 38° C., and fixed, washed with water and dried according to a known manner.

| Developing Solution | |
|---|---|
| Sodium sulfite | 75 g |
| Sodium hydrogencarbonate | 7 g |
| Hydroquinone | 40 g |
| 1-Phenyl-4,4-dimethyl-3-pyrazolidone | 0.4 g |
| Sodium bromide | 3 g |
| 5-Methylbenzotriazole | 0.8 g |
| Disodium ethylenediaminetetraacetate | 0.8 g |
| 3-Diethylamino-1,2-propanediol | 20 g |
| Water to make | 1 liter |
| | (pH = 11.4) |

TABLE 2

| Light-Sensitive Sheet | Compound No. | $D_{max}$ | $D_{min}$ | Gamma | Relative Sensitivity S-0.2*** | Dye Transfer Rate (50% Transfer Time) (sec) | Remark |
|---|---|---|---|---|---|---|---|
| 5 | blank | 1.98 | 0.30 | 1.1 | 0 | 57 | Comparison |
| 6 | 3 | 2.11 | 0.30 | 1.7 | +0.21 | 49 | Invention |
| 7 | 6 | 2.05 | 0.30 | 1.4 | +0.15 | 51 | " |
| 8 | 13 | 2.07 | 0.30 | 1.45 | +0.17 | 52 | " |

Note:
***The same as defined in Table 1.

EXAMPLE 3

A silver halide emulsion comprising 80 mol% of silver chloride, 19.5 mol% of silver bromide and 0.5 mol% of silver iodide was subjected to gold sensitization and sulfur sensitization in a usual manner. The emulsion contained 45 wt% of gelatin based on the silver halides. To the emulsion were added 5-[3-(δ-sulfobutyl)-5-chloro-2-oxazolidilidene]-1-hydroxyethoxyethyl-3-(2-pyridyl)-2-thiohydantoin potassium salt (spectral sensitizer), sodium dodecylbenzenesulfonate (surface active agent) and a polymer latex described in Preparation Example 3 of U.S. Pat. No. 3,525,620. Thereafter, 1,2-bis-(vinylsulfonylacetamido)ethane (hardener) was added thereto in an amount of 2.6 wt% based on the total dried gelatin including the gelatin contained in the hereinafter described insensitive upper layer. Further, a compound indicated in Table 3 was added to the mixture as a methanolic solution in the indicated amount to prepare a coating composition for a light-sensitive silver halide emulsion layer.

Separately, sodium dodecylbenzenesulfonate (surface active agent) and a polymethyl methacrylate latex having an average particle size of 3.0 to 4.0μ (matting Evaluations were made on relative sensitivity, gamma and dot quality, and the results are shown in Table 3. In Table 3, the relative sensitivities are relative values of the reciprocals of exposure doses that give a density of 1.5. The dot quality was visually evaluated according to four scales A to D, wherein A represents the best quality; B represents a practically usable quality; C represents a quality of no practical use; and D represents the worst quality.

TABLE 3

| Sample No. | Compound No. | Coverage (mol/mol-Ag) | Relative Sensitivity | Gamma | Dot Quality |
|---|---|---|---|---|---|
| 1 | none | — | 100 | 5 | D |
| 2 | 2 | 5.5 × 10⁻⁴ | 200 | 15 | A |
| 3 | 4 | " | 200 | 12 | A |
| 4 | 12 | " | 150 | 10 | B |

As is apparent from Table 3, the compounds of the present invention noticeably increase the sensitivity and contrast and produce good dot qualities.

While the invention has been described in detail with reference to specific embodiments thereof, it will be apparent to one skilled in the art that various changes and modifications can be made therein without departing from the spirit and scope thereof.

What is claimed is:

1. A silver halide photographic light-sensitive material which contains, in at least one layer thereof, a compound capable of releasing a fogging agent upon an oxidation-reduction reaction with an oxidation product of a developing agent under an alkaline condition during development processing, wherein said compound is a compound represented by the formula (I), (II), (III), (IV), (V) and (VI):

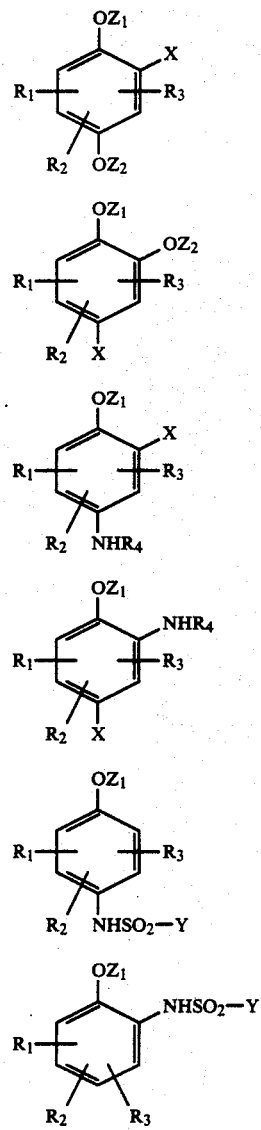

wherein $R_1$, $R_2$ and $R_3$, which are the same or different, each represents a hydrogen atom, a halogen atom, an alkyl group, an aryl group, an alkoxy group, an aryloxy group, an alkylthio group, an arylthio group, a cyano group, an alkoxycarbonyl group, a carbomoyl group a sulfamoyl group, a carboxyl group, a sulfo group, a sulfonyl group, an acyl group, a cyano group, a carbonamido group, a sulfonamido group or a heterocyclic group; or $R_1$ and $R_2$ are bonded to each other to form a benzene ring or a 5- to 7-membered heterocyclic ring; $R_4$ represents an alkyl group, an aryl group, an acyl group, a carbomoyl group, a sulfonyl group or a sulfamoyl group; $Z_1$ and $Z_2$, which are the same or different, each represents a hydrogen atom or a group capable of being removed by hydrolysis under an alkaline condition; X represents a group which exhibits a fogging effect in a developing solution when released; and Y represents a group which exhibits a fogging effect in a developing solution when released as $Y-SO_2NH_2$ or its anion, wherein Y represents a reducing group, a group capable of action on a silver halide during development to form a developable silver sulfide center or a quaternary salt, wherein Y represents a group having the partial structure of hydrazine, hydrazide, hydrazone, hydroxylamine, polyamine, enamine, hydroquinone, catechol, p-aminophenol, o-aminophenol, aldehyde or acetylene, a group having the partial structure of thiourea, thioamide, thiocarbamate, dithiocarbamate, thiohydantoin or rhodanine, or a tetrazolium salt, wherein X has the formula (X):

wherein TIME represents a timing group which releases $-L_1(L_2)_nA$ subsequently to the release of X, m represents 0 or 1; $L_1$ represents a group which is releasable for the release of X due to an oxidation-reduction reaction between compounds (I) and (IV) and a developing agent oxidation product under an alkaline condition when m is 0, or a group releasable from TIME of the released X when m is 1, wherein $L_1$ represents an aryloxy group, a heterocyclic oxy group, an arylthio group, a heterocyclic thio group or an azolyl group; $L_2$ represents a divalent linking group; n represents 0 or 1; and A represents a group which substantially exhibits a fogging effect to a silver halide emulsion when X exists in a developing solution in the form of $X^-$ or $X-H$.

2. A silver halide photographic light-sensitive material as claimed in claim 1, wherein $Z_1$ and $Z_2$ each represents a hydrogen atom, an acyl group, a sulfonyl group, an alkoxycarbonyl group, a carbamoyl group, an oxalyl group or a group represented by the formula (VII), (VIII) or (IX):

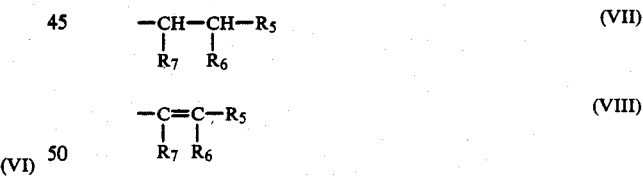

wherein $R_5$ represents an acyl group, a sulfonyl group, a cyano group, a carbamoyl group, a sulfamoyl group, an alkoxycarbonyl group, a nitro group, a carboxyl group, a sulfo group or an ammoniumyl group; and $R_6$ and $R_7$, which may be the same or different, each represents a hydrogen atom, an alkyl group or the same groups as those enumerated for $R_5$; or $R_5$ and $R_7$ is bonded to each other to form a 5- to 7-membered ring;

wherein $R_8$ represents a hydrogen atom, an alkyl group or an aryl group; V represents

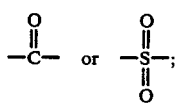

Q represents, when taken together with

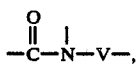

a non-metallic atomic group necessary to form a 5- or 6-membered ring.

3. A silver halide photographic light-sensitive material as claimed in claim 2, wherein $Z_1$ and $Z_2$ each represents an acetyl group, a chloroacetyl group, a dichloroacetyl group, a trifluoroacetyl group, a benzoyl group, a p-nitrobenzoyl group, a methanesulfonyl group, a benzenesulfonyl group, a methoxycarbonyl group, a phenoxycarbonyl group, an ethylcarbamoyl group, a phenylcarbamoyl group, a pyruvoyl group, a methoxalyl group, a phenyloxamoyl group, or a group of the formula

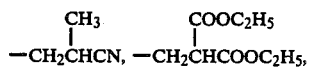

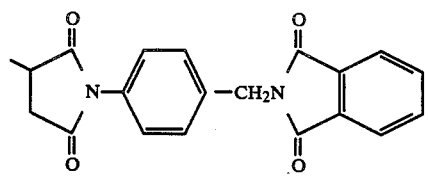

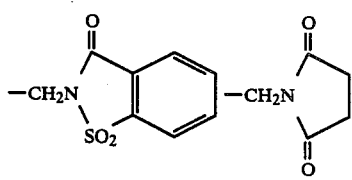

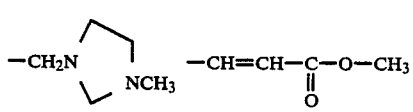

or 

4. A silver halide photographic light-sensitive material as claimed in claim 1, wherein $L_1$ represents a group of the formula

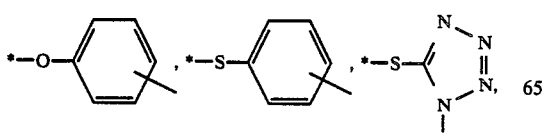

-continued

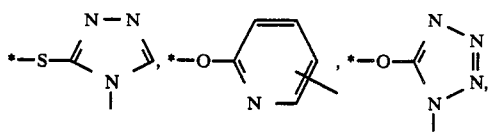

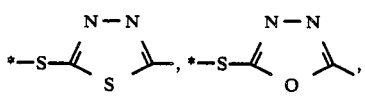

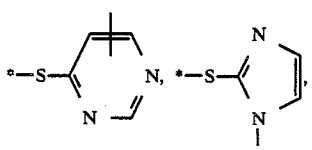

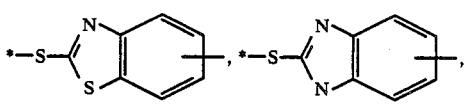

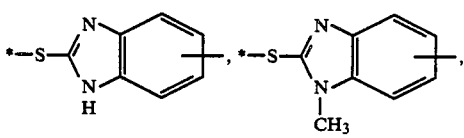

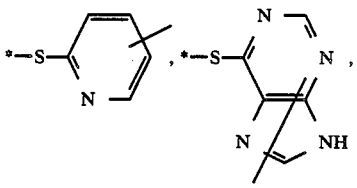

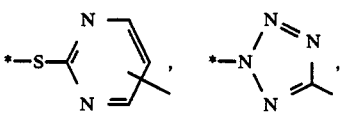

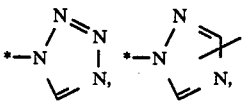

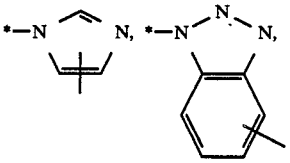

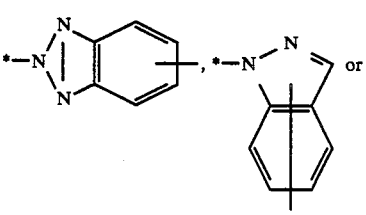

-continued

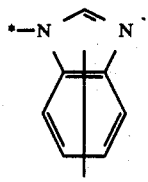

wherein the mark * represents the bonding position to —TIME)$_m$.

5. A silver halide photographic light-sensitive material as claimed in claim 1, wherein L$_2$ represents an alkylene group, an alkenylene group, an arylene group, a divalent heterocyclic group, —O—, —S—, an imino group, —COO—, —CONH—, —NHCONH—, —NHCOO—, —SO$_2$NH—, —CO—, —SO$_2$—, —SO—, —NHSO$_2$NH— or a combination thereof.

6. A silver halide photographic light-sensitive material as claimed in claim 1, wherein A represents a reducing group, a group capable of acting on a silver halide during development to form a developable silver sulfide center or a quaternary salt.

7. A silver halide photographic light-sensitive material as claimed in claim 6, wherein A represents a group having the partial structure of hydrazine, hydrazide, hydrazone, hydroxylamine, polyamine, enamine, hydroquinone, catechol, p-aminophenol, o-aminophenol, aldehyde or acetylene, a group having the partial structure of thiourea, thioamide, thiocarbamate, dithiocarbamate, thiohydantoin or rhodanine, or a tetrazolium salt.

8. A silver halide photographic light-sensitive material as claimed in claim 7, wherein A is a group represented by the formula (XI):

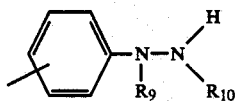 (XI)

wherein R$_9$ represents a hydrogen atom, an acyl group or an alkoxycarbonyl group; and R$_{10}$ represents an acyl group, a sulfonyl group, a carbamoyl group, an alkoxycarbonyl group, a sulfamoyl group, a thioacyl group, a thiocarbamoyl group or a heterocyclic group.

9. A silver halide photographic light-sensitive material as claimed in claim 1, wherein X is a group represented by the following formulae:

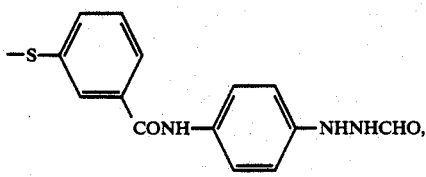

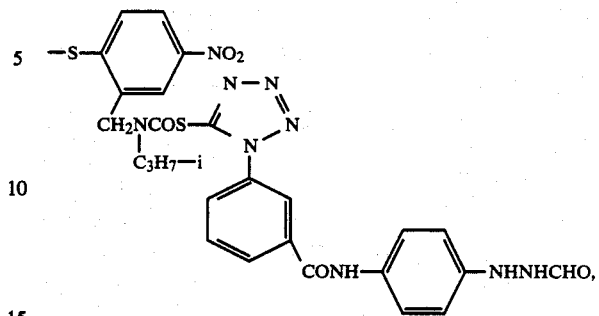

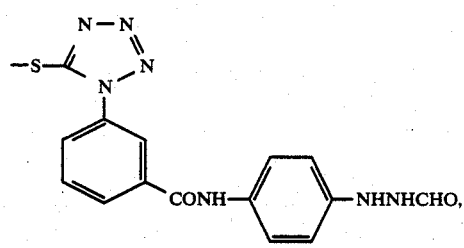

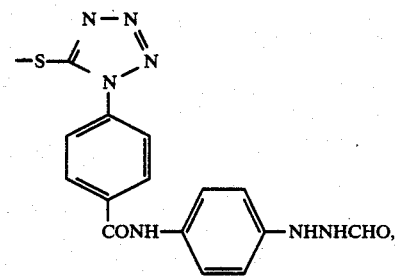

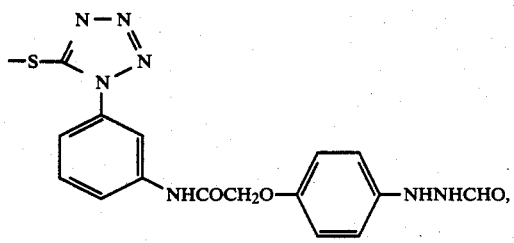

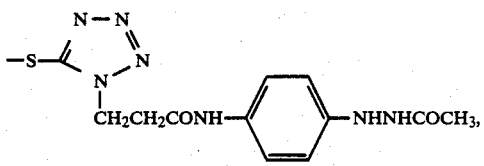

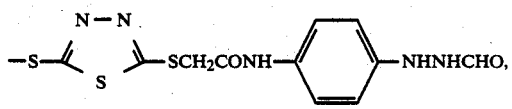

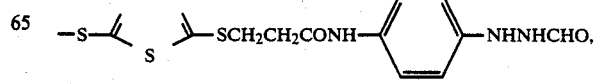

-continued

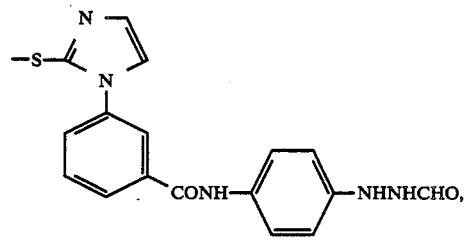

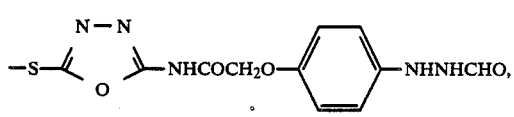

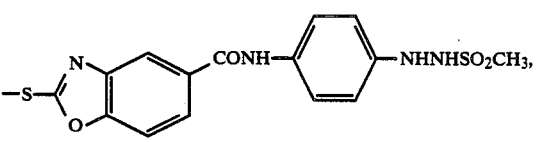

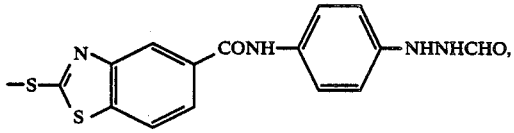

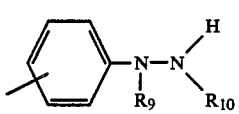

-continued

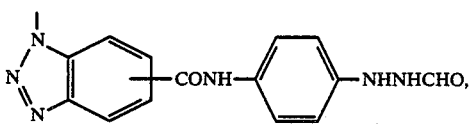

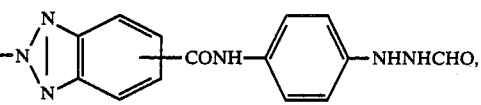

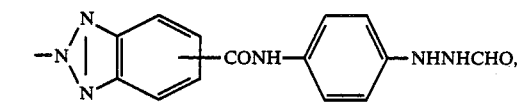

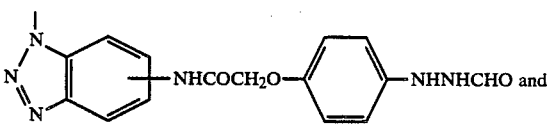

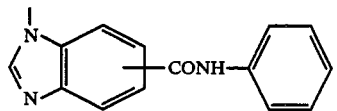

10. A silver halide photographic light-sensitive material as claimed in claim 1, wherein Y is a group represented by the formula (XI):

$$\text{(XI)}$$

wherein $R_9$ represents a hydrogen atom, an acyl group or an alkoxycarbonyl group; and $R_{10}$ represents an acyl group, a sulfonyl group, a carbamoyl group, an alkoxycarbonyl group, a sulfamoyl group, a thioacyl group, a thiocarbamoyl group or a heterocyclic group.

11. A silver halide photographic light-sensitive material as claimed in claim 1, wherein said compound is present in an amount of $10^{-8}$ to 1 mol per mol of silver.

* * * * *